(12) United States Patent
Voskoboynikov et al.

(10) Patent No.: US 8,288,602 B2
(45) Date of Patent: Oct. 16, 2012

(54) SYNTHESIS OF SUBSTITUTED FLUORENE LIGANDS

(75) Inventors: Alexander Z. Voskoboynikov, Moscow (RU); Artyom Y. Le Bedev, Moscow (RU); Andrey F. Asachenko, Moscow (RU); Abbas Razavi, Mons (BE)

(73) Assignee: Total Petrochemicals Research Feluy, Seneffe (Feluy) (BE)

( * ) Notice: Subject to any disclaimer, the term of this patent is extended or adjusted under 35 U.S.C. 154(b) by 383 days.

(21) Appl. No.: 12/294,523

(22) PCT Filed: Mar. 28, 2007

(86) PCT No.: PCT/RU2007/000148
§ 371 (c)(1),
(2), (4) Date: Sep. 22, 2010

(87) PCT Pub. No.: WO2007/111537
PCT Pub. Date: Oct. 4, 2007

(65) Prior Publication Data
US 2011/0009683 A1    Jan. 13, 2011

(30) Foreign Application Priority Data
Mar. 28, 2006 (WO) ................ PCT/RU2006/000148

(51) Int. Cl.
*C07C 13/567* (2006.01)
(52) U.S. Cl. ........ 585/411; 585/400; 585/407; 585/410; 585/446; 585/459
(58) Field of Classification Search ................ 585/400, 585/407, 410, 411, 446, 459
See application file for complete search history.

(56) References Cited

U.S. PATENT DOCUMENTS

| | | | | |
|---|---|---|---|---|
| 3,303,224 A | * | 2/1967 | Crump | 570/206 |
| 3,324,192 A | * | 6/1967 | Roebuck et al. | 585/460 |
| 5,347,026 A | | 9/1994 | Patsidis et al. | |
| 6,037,501 A | * | 3/2000 | Saito et al. | 568/300 |
| 6,117,371 A | * | 9/2000 | Mack | 252/609 |
| 7,094,938 B1 | | 8/2006 | Marin et al. | |

OTHER PUBLICATIONS

Colon, et al., "Coupling of Aryl Chlorides by Nickel and Reducing Metals" in J. Org. Chem., 1986, 51, 2627-2637—1986, month unknown.*
Paul, Gitendra C., et al., "Synthesis of 3,6-DI-(tert-Butyl)Fluorene by Nickel(0) Catalyzed Coupling of Aryl Halides," Organic Preparations and Procedures Intl., vol. 30, No. 2, 1998, pp. 222-225, 1998.

* cited by examiner

*Primary Examiner* — In Suk Bullock
*Assistant Examiner* — Bradley Etherton

(57) ABSTRACT

The present invention describes a cost-efficient method for preparing di-substituted fluorenes in high yield.

15 Claims, No Drawings

SYNTHESIS OF SUBSTITUTED FLUORENE LIGANDS

The present invention relates to the high yield synthesis of substituted fluorenes.

The most common method for preparing 3,6-disubstituted fluorenes used as starting material the costly 2,2'-diiodine-4,4'-di-substituted-diphenylmethane. 3,6-Disubstituted fluorene was produced by reacting about 0.5 equivalents of the nickelum salt, close to 1 equivalent of extremely expensive and unhealthy $PPh_3$, at least 1.5 equivalent of expensive $Et_4NI$, and at least 1.5 equivalent of zinc powder. The reaction was carried out in tetrahydrofuran (THF) at a temperature of about 70° C. and for a period of time of about 7 hr. This procedure was long, tedious, costly and hazardous to health.

Prior art document "Synthesis of 3,6-di-(tert-butytl)fluorine by nickel catalysed coupling of aryl halides.", by Gitendra C. P. and Gajewski J. J., In organic preparations and procedures intl., vol. 30, no 2, 222-225, 1998, discloses a process for making fluorine starting from diphenylmethane and using diiodo intermediates.

There is thus a need to develop processes capable to produce substituted fluorenes in high yield.

It is an aim of the present invention to provide a method for preparing substituted fluorenes.

It is also an aim of the present invention to provide said compounds in high yield.

It is another aim of the present invention to provide a method that is efficient and economical to prepare fluorenes.

Accordingly, the present invention provides a method for preparing substituted fluorenes that comprises the steps of:

I) alkylation of diphenylmethane with at least 2 equivalents of alkylating agent of general formula

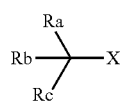

wherein

X is a halogen selected from Cl, Br or I;

$R^a$, $R^b$ and $R^c$ are each independently selected from alkyl, aryl, heteroaryl, cycloalkyl or alkenyl having from 1 to 20 carbon atoms, with the restriction that a carbon atom from each of $R^a$, $R^b$ and $R^c$ is directly attached to the quaternary carbon atom;

in presence of Lewis acid with appropriate isolation procedure;

II) bromination of step I product with 2.01 to 2.05 equivalents of bromine at temperature slightly below room temperature in presence of a Lewis acid or a metal that is able to give a Lewis acid in the reaction medium, followed by an isolation procedure that comprises removing excess bromine with appropriate reagent and recrystallysation after a standard work-up;

III) reaction of the product resulting step II with a reducing agent in the presence of a catalyst consisting of a ligand of general formula

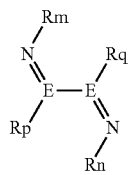

wherein $R^m$, $R^n$ $R^p$ and $R^q$ are the same or different and are each independently selected from hydrocarbyl having from 1 to 30 carbon atoms or any organic substituent with the restriction that a halogen cannot be directly attached to N and wherein any two consecutive R's can be joined to make a ring and wherein E's are the same or different and are each independently selected from C, N, P or B;

and a compound of any Group 10 metal, preferably, an anhydrous salt of Group 10 metal and optionally, based upon the type and amount of catalyst, in the presence of a salt of HCl, HBr or HI, Step I.

Preferably, in compound $CXR^aR^bR^c$ in step I X is chlorine and $R^a$, $R^b$ and $R^c$ are each independently alkyl groups having from 1 to 6 carbon atoms. More preferably they are the same, yet more preferably they are the same and they are tBu. Alternatively, another preferred compound is t-BuCl. The most preferred positions for the substituents on the diphenylmethane are positions 4 and 4'. Small substituents such as methyl groups can occupy the 2 and 2' positions and are thus not preferred.

Preferably, the Lewis acid used in stage I can be selected from $AlX_3$ wherein X is Cl, Br, F, I, OR, $CR_3$, $NR_2$, or OC(O)R, wherein each R can be independently selected from an alkyl group having from 1 to 6 carbon atoms. More preferably, it is $AlCl_3$. The amount of Lewis acid can typically range from 0.01 to 5 wt %, preferably from 1 to 3 wt %, based on the weight of substituted diphenylmethane in step I.

Said compound is crystallised preferably from isopropyl alcohol or from hexanes, more preferably from isopropyl alcohol In the purification step, at the end of step I, no washing is necessary before the recrystallisation because some aluminium contaminant should preferably be left in the di-substituted-diphenylmethane compound. Actually, these aluminium (III) impurities serve as an additional catalyst on the bromination step below (step II).

The preferred resulting product of step I is 4,4'-di-substituted-diphenylmethane.

Step II.

The preferred solvent is $CH_2Cl_2$.

The amount of bromine that is added to the system is narrowly limited from 2.01 to 2.05 equivalents with respect to the di-substituted diphenylmethane in order to obtain a clean product with Br occupying positions 2 and 2' of the di-substituted compound. If bromine is added in excess, it occupies other positions and can possibly displace the substituents and prevent crystallisation of the final product. If added in too small amount, the final product does not crystallise.

Preferably, the catalyst is Fe. The catalyst is placed in the reaction vessel with the solvent and the di-substituted-diphenylmethane, and the bromine in solvent is added slowly to the vessel that is maintained below room temperature, preferably between 10 and 20° C.

The resulting product is washed with a solution that can trap $Br_2$. Preferably, it is a solution of $Na_2SO_3$ in water.

The resulting product is separated, dried over a drying agent, evaporated and crystallised from EtOH or hexanes, preferably from EtOH.

The preferred resulting product of step II is 2,2'-dibromo-4,4'-di-substituted-diphenylmethane.

Step III.

The product resulting from step II is added to an aprotic solvent, preferably an etheric solvent, more preferably THF.

The ligand can be selected from a great variety of compounds, but it is preferred that substituents R''' and R'', directly attached to the nitrogen atoms be sterically hindered substituents. More preferably, they are secondary or tertiary hydrocarbyl having at least 3 and up to 30 carbon atoms. Preferably, both E's are the same and are carbon atoms. The amount of ligand is of from 0.01 up to 20 mol %.

The reducing agent can be an organic reducing agent or zinc. Preferably it is zinc in powder form. One to two equivalents of the reducing agent with respect to the diphenylmethane compound are typically used, preferably, 1.5 equivalents.

A compound of Group 10 metal as well as a salt of HCl, HBr or HI are then added to the system.

Preferably, the compound of Group 10 metal is an anhydrous salt of Ni, Pd or Pt, more preferably of Ni. More preferably it is an anhydrous halogenide such as for example $NiCl_2$ or $NiBr_2$. The most preferred compound is $NiCl_2$. The amount of compound of Group 10 metal necessary is of from 0.01 up to 20 mol %. The ligand and compound of Group 10 metal are generally used in the same molar amounts.

Among the preferred optional salt of HCl, HBr or HI, one can cite for example from $Et_4NI$, KBr, NaBr, KI, NaI, CsBr. It is more preferred to select from these salts those for which ionic radii (both cation and anion) are as large as possible. The most preferred salt is $Et_4NI$.

The amount of salt of HCl, HBr or HI necessary in the reaction depends upon the amount of catalyst used and upon the nature of the salt used. If the amount of catalyst used is larger than 10 mol %, no salt needs to be added.

The reaction is carried out at reflux, at a temperature ranging from 50 to 100° C., preferably at a temperature of about 70° C. and for a period of time of from 1 to 3 hours, preferably about 1.5 hours.

EXAMPLES

Example 1

Preparation of 4,4'-Di-tert-butyldiphenylmethane

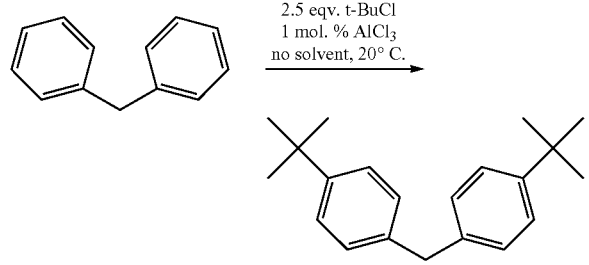

In a 500-ml flask, to a mixture of 16.8 g (100 mmol) of diphenylmethane and 21.3 g (230 mmol) of tert-butyl chloride, 67 mg (0.5 mmol) of anhydrous $AlCl_3$ were added, at room temperature, under vigorous stirring, resulting in immediate HCl gas emission. The reaction mixture turned red. After 5 min, a second portion of 67 mg (0.5 mmol) of $AlCl_3$ were added. After 5 min of vigorous stirring, the reaction mixture became hard. After about 1 h, the hard mass obtained was recrystallised from about 100 mL of hot isopropanol. The crystalline product precipitated from this solution at a temperature of −30° C. after a period of time of about 2 to 3 h. It was separated, washed with 50 ml of cold isopropanol, and dried in vacuum under a reduced pressure of 10 to 20 mm Hg. 19.6 g of product were obtained with a yield of 70%. The procedure was repeated with a yield ranging between 67 and 74%.

Anal. for $C_{21}H_{28}$: Calculated: C, 89.94; H, 10.06. Found: C, 89.86; H, 10.03.

$^1$H NMR ($CDCl_3$): δ 7.31 (d, J=8.4 Hz, 4H), 7.13 d, J=8.4 Hz, 4H), 3.92 (s, 2H), 1.30 (s, 18H).

$^{13}C\{^1H\}$ NMR ($CDCl_3$): δ 148.7, 138.2, 128.5, 125.2, 41.0, 34.3, 31.4.

Preparation of 2,2'-Dibromo-4,4'-di-tert-butyldiphenylmethane

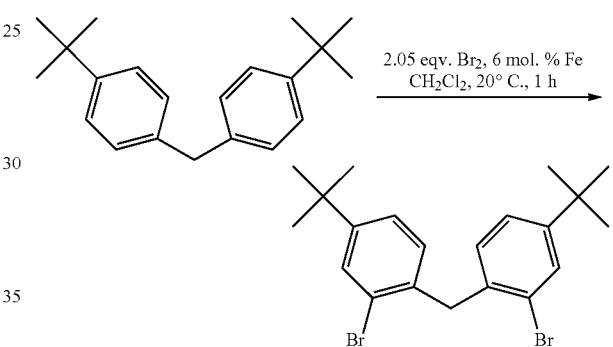

In a three-necked round-bottom 250-ml flask equipped with a thermometer, a dropping funnel with a pressure-equalising bypass, a drying tube (with $CaCl_2$), and a magnetic stirring bar, to a mixture of 14.0 g (50 mmol) of 4,4'-di-tert-butyldiphenylmethane, 168 mg (3 mmol) of iron powder, and 50 ml of dichloromethane, a solution of 16.8 g (105 mmol) of bromine in 25 ml of dichloromethane was added dropwise under vigorous stirring for about ½ h. To obtain the product in good yield, the temperature of the reaction mixture had to be maintained between 10 and 20° C., so, when necessary a cold water bath was used to cool the reaction mixture. Next, the reaction mixture was additionally stirred for 1 hour at room temperature. Then, the mixture obtained was washed twice with 75 ml of a saturated solution of $Na_2SO_3$ to remove the bromine traces. The organic layer was separated, and the aqueous layer was additionally washed with 75 ml of dichloromethane. The combined organic extract was dried over anhydrous $CaCl_2$ and evaporated to dryness. The crystalline mass obtained was dissolved in about 50 ml of hexanes. This hexane solution was passed through a layer of Silica Gel 60 (diameter ca. 50 mm, length ca. 30 mm) to remove inorganic salts and some polymeric impurities. Additionally, the silica gel layer was washed with 300-400 ml of hexanes. The combined hexanes elute was evaporated to dryness. The residue was crystallised from about 200 ml of hot ethanol (96%). Crystals precipitated at a temperature of −30° C. and were separated, washed with 50 ml of cold ethanol, and dried in vacuum (1-2 mm Hg). 14.9 g of yellowish crystalline product was obtained with a yield of 68%.

Anal. Calcd for C$_{21}$H$_{26}$Br$_2$: C, 57.55; H, 5.98. Found: C, 57.65; H, 5.91.

$^1$H NMR (CDCl$_3$): δ 7.59 (d, J=2.0 Hz, 2H), 7.23 (dd, J=2.0 Hz, J=8.1 Hz, 2H), 6.92 (d, J=8.1 Hz, 2H), 4.13 (s, 2H), 1.30 (s, 18H).

$^{13}$C{$^1$H} NMR (CDCl$_3$): δ 151.4, 136.0, 130.3, 129.7, 124.8, 124.6, 41.0, 34.5, 31.2.

Preparation of ligand 2,4,4-Trimethyl-N-((E,2E)-2-{[(E)-1,1,3,3-tetramethylbutyl]imino}ethylidene)-2-pentanamine (L1)

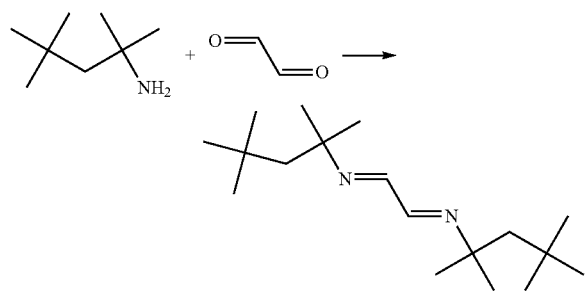

In a round-bottom 2000-ml flask, a mixture of 56.3 g (0.39 mmol) of 40% glyoxale, 100 g (0.78 mmol) of tert-octylamine, and 1200 cm$^3$ of water were stirred for 4 h at room temperature. The resulting precipitate was separated and washed with about 200 ml of cold water. The white powder was dissolved in 300 ml of dichloromethane. The solution was dried over Na$_2$SO$_4$ and then evaporated until dry. 101 g of white solid were obtained with a yield of 93%.

Anal. for C$_{18}$H$_{36}$N$_2$: Calculated C, 77.08; H, 12.94. Found: C, 76.92; H, 13.05.

$^1$H NMR (CDCl$_3$): δ 7.94 (s, 2H), 1.69 (s, 4H), 1.29 (s, 12H), 0.92 (s, 18H).

$^{13}$C{$^1$H} NMR (CDCl$_3$): δ 157.5, 61.9, 55.9, 32.0, 31.6, 29.31.

Preparation of 3,6-Di-tert-butylfluorene

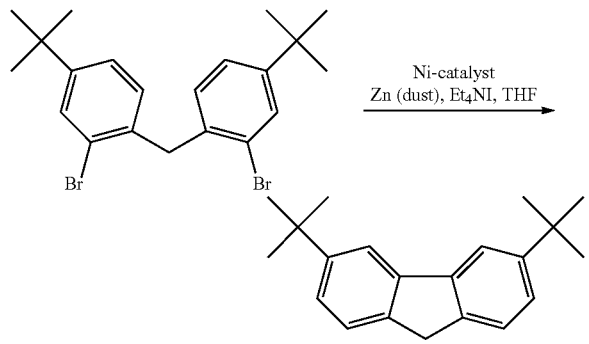

In a three-necked round-bottom 1000-ml flask, 9.83 g (150 mmol) of the activated zinc dust that had been previously washed with 2% HCl, water, ethanol, then with ether, dried in vacuum and stored in nitrogen atmosphere, 43.8 g (100 mmol) of 2,2'-dibromo-4,4'-di-tert-butyldiphenylmethane, and 5.02 g (20 mmol) of Et$_4$NI were placed. This flask was evacuated and then filled with dry nitrogen. To this mixture, 600 ml of THF and a mixture of 840 mg (3 mmol) of the 2,4,4-trimethyl-N-((E,2E)-2-{[(E)-1,1,3,3-tetramethylbutyl]imino}ethylidene)-2-pentanamine and 924 mg (3 mmol) of NiBr$_2$(DME) prepared in the glove box were added. The resulting mixture was slightly heated under vigorous stirring with a magnetic stirrer. After the reaction started (after 2 to 3 min), the external heating was interrupted since the reaction is exothermic. However, this mixture was refluxed for at least 1 h. Next, the resulting mixture was cooled to room temperature and evaporated to dryness using the rotary evaporator. To the residue, 300 ml of saturated aqueous NH$_4$Cl and 300 ml of hexanes were added. This mixture was stirred vigorously to achieve complete extraction of the product with hexanes. Next, the organic layer was separated; the aqueous layer was additionally extracted with 2×300 ml of hexanes. The combined extract was dried over Na$_2$SO$_4$ and then passed through short column with Silica Gel 60 (40-63 μm, diameter about 50 mm, length about 50 mm). The silica gel layer was additionally washed with 300 ml of hexanes. The combined elute was evaporated using the rotary evaporator. The residue became hard after an additional drying in vacuum (1-2 mm Hg) of the colorless oil obtained. 29.8 g of white solid of the title product were obtained with a yield of 98%.

Anal. Calcd for C$_{21}$H$_{28}$: C, 90.59; H, 9.41 Found: C, 90.45; H, 9.50.

$^1$H NMR (CDCl$_3$): δ 7.81 (d, J=1.5 Hz, 2H), 7.45 (d, J=8.0 Hz, 2H), 7.33 (dd, J=1.5 Hz, J=8.0 Hz, 2H), 4.13 (s, 2H), 1.30 (s, 18H).

$^{13}$C{$^1$H} NMR (CDCl$_3$): δ 149.8, 141.8, 140.8, 124.5, 123.8, 116.3, 36.0, 34.8, 31.7.

Example 2

Other ligands L2 to L5 were prepared using a condensation reaction of a primary amine with a dicarbonyl compound.

Preparation of N-((E,2E)-2-{[(E)-1,1-Dimethylethyl]imino}ethylidene)-2-methyl-2-propanamine (L2)

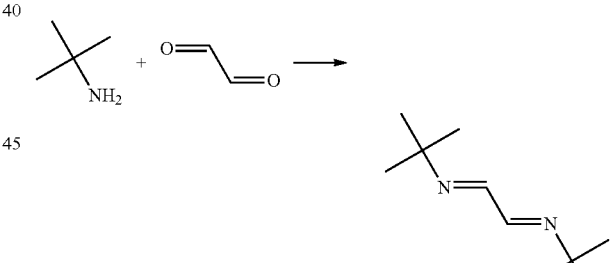

In a round-bottom 250-ml flask, to a mixture of 36.3 g (0.25 mmol) of 40% glyoxale and 150 ml of water, 38.5 g (0.50 mmol) of tent-butylamine were added under vigorous stirring. This reaction was highly exothermic, and a light oil layer was formed. The resulting mixture was cooled to room temperature, and the organic layer became hard. The solid formed was separated and washed with about 200 ml of cold water. This solid was dissolved in 200 ml of dichloromethane. The solution was then dried over Na$_2$SO$_4$ and evaporated to dryness. 41.2 g of white crystalline product were obtained with a yield of 98%.

Anal. for C$_{10}$H$_{10}$N$_2$: Calculated: C, 71.37; H, 11.98. Found: C, 71.25; H, 12.09.

$^1$H NMR (CDCl$_3$): δ 7.95 (s, 4H), 1.27 (s, 18H)

$^{13}$C{$^1$H} NMR (CDCl$_3$): δ 157.5, 57.8, 29.1. .

Preparation of N-[(E,2E)-2-(1-Adamantylimino)ethylidene]-1-adamantanamine (L3)

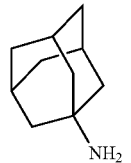 +  →

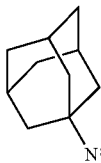

In a round-bottom 500-ml flask, a mixture of 11.3 g (60 mmol) of 1-adamantylamine hydrochloride, 205 ml (30 mmol) of 0.292 M NaOH, and 8.70 g (30 mmol) of 40% glyoxale was stirred for 5 h. The product was extracted with 4×200 ml of ether. The combined extract was dried over $Na_2SO_4$ and evaporated to dryness. The solid obtained was recrystallised from 200 ml of hexanes. The product obtained was again recrystallised from a new portion of 200 ml of hexanes. The crystalline solid obtained was dried in vacuum. 7.81 g (80%) of white solid were obtained with a yield of 80%.

Anal. for $C_{22}H_{32}N_2$. Calculated: C, 81.43; H, 9.94. Found: C, 81.47; H, 9.97.

$^1$H NMR (CDCl$_3$): δ 7.93 (s, 2H), 2.15 (s, 6H), 1.77-1.63 (m, 24H).

$^{13}$C{$^1$H} NMR (CDCl$_3$): δ 157.8, 58.5, 42.7, 36.4, 29.4.

Preparation of N-[(E,2E)-2-(Cyclohexylimino)ethylidene]cyclohexanamine (L4)

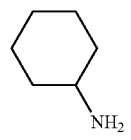 +  →

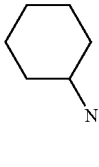

In a round-bottom 500-ml flask, a mixture of 12.8 g (129 mmol) of cyclohexylamine, 23.4 g (65 mmol) of 40% glyoxale, and 50 ml of water was stirred for 2 days. The resulting precipitate was separated and washed with 50 ml of cold water. The solid was dissolved in 50 ml of dichloromethane. This solution was dried over $Na_2SO_4$ and evaporated to dryness. The residue was recrystallised from 200 ml of ether. 10.3 g of white solid were obtained with a yield of 72%.

Anal. for $C_{14}H_{24}N_2$. Calculated: C, 76.31; H, 10.98. Found: C, 76.22; H, 11.00.

$^1$H NMR (CDCl$_3$): δ 7.94 (s, 2H), 3.23-3.10 (m, 2h), 1.87-1.62 (m, 5H), 1.58-1.44 (m, 2H), 1.43-1.15 (m, 3H).

$^{13}$C{$^1$H} NMR (CDCl$_3$): δ 159.8, 69.1, 33.7, 25.2, 24.3.

Preparation of N-{(1E,2E)-2-[(2,6-Diisopropylphenyl)imino]acenaphthylenylidene}-2,6-diisopropylaniline (L5)

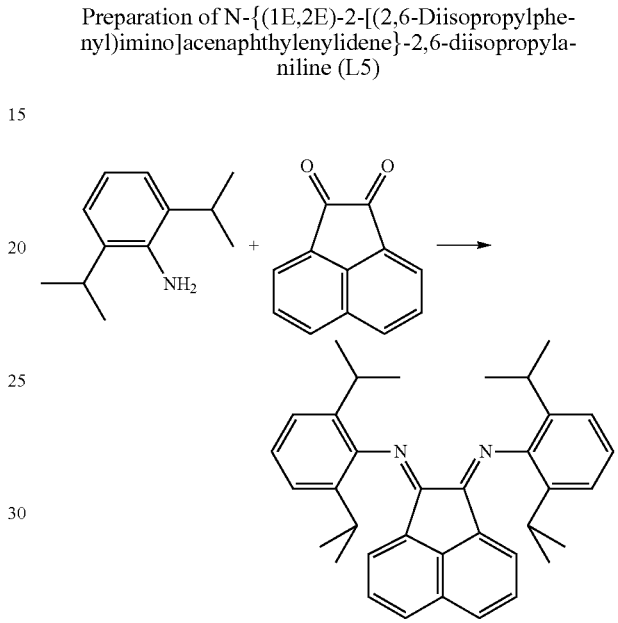

A mixture of 1.82 g (10 mmol) of acenaphtoquinone, 3.54 g (20 mmol) of 2,6-diisopropylaniline, and 40 ml of glacial acetic acid was refluxed for 2 h and then stirred for 12 h at room temperature. The resulting precipitate was separated, washed with 20 ml of cold water, and dried under vacuum. 3.89 g of dark-yellow solid were obtained with a yield of 78%.

Anal. for $C_{36}H_{40}N_2$. Calculated: C, 86.35; H, 8.05. Found: C, 86.43; H, 8.14.

$^1$H NMR (CDCl$_3$): δ 7.87 (d, J=8.1 Hz, 2H), 7.36 (dd, J=8.1 Hz, J=7.2 Hz 2H), 7.31-7.20 (m, 6H), 6.64 (d, J=7.2 Hz, 2H), 3.04 (hept, J=6.8 Hz, 4H), 1.24 (d, J=6.9 Hz, 12H), 0.97 (d, J=6.9 Hz, 12H).

$^{13}$C{$^1$H} NMR (CDCl$_3$): δ 161.0, 147.5, 140.8, 135.4, 131.1, 129.5, 128.8, 127.8, 124.3, 123.4, 123.3, 28.6, 23.4, 23.1.

Ligand L6 of formula

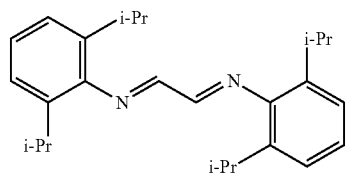

is known and is commercially available.

Example 3

The substituted fluorene was prepared following the same general method as that described in Example 1 with ligands L1 to L6 under various conditions that are summarised in Table 1. For all preparations, the reducing agent was zinc powder. The yield for each preparation reaction is also given in Table 1.

TABLE 1

| Ni-Catalyst | mol % Ni | Ligand L | mol % L | Salt | mol % salt | T (° C.) | Time (h) | yield % |
|---|---|---|---|---|---|---|---|---|
| NiCl$_2$ | 20 | L1 | 20 | Et$_4$NI | 100 | 70 | 15 | >99 |
| NiBr$_2$ (DME) | 20 | L1 | 20 | Et$_4$NI | 100 | 25 | 15 | >99 |
| NiBr$_2$ (DME) | 20 | L1 | 20 | Et$_4$NI | 100 | 25 | 2.5 | >99 |
| NiBr$_2$ (DME) | 3 | L1 | 3 | Et$_4$NI | 5 | 70 | 15 | >99 |
| NiCl$_2$ | 20 | L2 | 20 | Et$_4$NI | 100 | 70 | 15 | >99 |
| NiBr$_2$ (DME) | 20 | L2 | 20 | Et$_4$NI | 100 | 25 | 15 | 57 |
| NiCl$_2$ | 10 | L2 | 10 | KBr | 100 | 70 | 15 | >99 |
| NiCl$_2$ | 10 | L2 | 10 | KI | 100 | 70 | 15 | >99 |
| NiCl$_2$ | 10 | L2 | 10 | Et$_4$NI | 100 | 70 | 15 | >99 |
| NiCl$_2$ | 10 | L2 | 10 | none | — | 70 | 15 | 95 |
| NiCl$_2$ | 3 | L2 | 3 | KBr | 20 | 70 | 15 | 54 |
| NiCl$_2$ | 3 | L2 | 3 | KI | 20 | 70 | 15 | 57 |
| NiCl$_2$ | 3 | L2 | 3 | Et$_4$NI | 20 | 70 | 15 | >99 |
| NiCl$_2$ | 20 | L3 | 20 | Et$_4$NI | 100 | 70 | 15 | >99 |
| NiBr$_2$ (DME) | 20 | L3 | 20 | Et$_4$NI | 100 | 25 | 15 | 77 |
| NiCl$_2$ | 20 | L4 | 20 | Et$_4$NI | 100 | 70 | 15 | >99 |
| NiBr$_2$ (DME) | 20 | L4 | 20 | Et$_4$NI | 100 | 25 | 15 | >99 |
| NiCl$_2$ | 20 | L5 | 20 | Et$_4$NI | 100 | 70 | 15 | 87 |

Example 4

Ligand L6 was used to evaluate the influence of changing the nature and amount of optional salt of HCl, HBr or HI in stage III.

For all examples, 20 mol % of NiCl$_2$ and ligand L6 were used, the reaction temperature was of 70° C. and the reaction time was of 15 hours.

The nature and amount of salt and the yield are reported in Table 2.

TABLE 2

| Salt | mol % of salt | Yield in % |
|---|---|---|
| Et$_4$NI | 100 | >99 |
| Et$_4$NI | 50 | 94 |
| Et$_4$NI | 20 | 91 |
| KBr | 100 | 62 |
| CsBr | 100 | >99 |
| Et$_4$NBr | 100 | 83 |
| n-Bu$_4$NBr | 100 | 82 |
| n-Bu$_4$NCl | 100 | 27 |
| n-Bu$_4$NBr | 200 | 23 |
| NaI | 100 | 63 |
| KI | 100 | 87 |
| none | — | 21 |
| LiBr | 100 | <1 |
| NaBr | 100 | 28 |
| 1:1 (mol.) mixture of NaBr + 15 − crown − 5 | 100 | 88 |
| 1:1 (mol.) mixture of Et$_4$NI + ZnBr$_2$ | 50 | 55 |

From this table, it can be concluded that the yield of the product increases with increasing size of the ions constituting the salt. It is thus preferred to use salts having both cation and anion as large as possible.

The invention claimed is:

1. A method for preparing substituted fluorenes that comprises the steps of:
   I. alkylating diphenylmethane with at least 2 equivalents alkylating agent of general formula

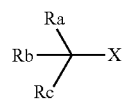

wherein
   X is a halogen selected from Cl, Br or I;
   Ra, Rb and Rc are each independently selected from alkyl, aryl, heteroaryl, cycloalkyl or alkenyl having from 1 to 20 carbon atoms, with the restriction that a carbon atom from each of Ra, Rb and Rc is directly attached to the carbon atom in the presence of a Lewis acid and crystallizing the alkylated product;
   II. brominating the step I product with 2.01 to 2.05 equivalents of bromine at between 10° C. and 20° C. in the presence of a Lewis acid or a metal that is able to give Lewis acid in the reaction medium, followed by washing with a solution and recrystallization after separation and drying;
   III. reacting the product resulting from step II with a reducing agent in the presence of a catalyst consisting of a ligand of general formula

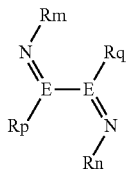

wherein
   Rm, Rn Rp and Rq are each independently selected from hydrocarbyl having from 1 to 30 carbon atoms or any organic substituent with the restriction that a halogen cannot be directly attached to N and wherein any two consecutive R's of the ligand can be joined to make a ring, and wherein E's are the same or different and are each independently selected from C, N, P or B;
   and
   a compound of a Group 10 metal.

2. The method of claim 1 wherein in complex CXRaRbRc, in step I, X is chlorine and Ra, Rb and Rc are each independently selected from alkyl having from 1 to 6 carbon atoms.

3. The method of claim 2 wherein Ra, Rb and Rc are the same and are tert-butyl.

4. The method of claim 1 wherein, in step I, the Lewis acid is AlCl$_3$.

5. The method of claim 1 wherein the amount of Lewis acid is of from 0.01 to 5 wt % based on the weight of all reactants in stage I.

6. The method of claim 1 wherein in step II the catalyst is Fe.

7. The method of claim 1 wherein, in the ligand of step III substituents Rm and Rn directly attached to nitrogen are independently selected from secondary or tertiary hydrocarbyls having between 3 and 30 carbon atoms.

8. The method of claim 1 wherein the reducing agent of step III is zinc in powder form.

9. The method of claim 1 wherein the final product is 3,6-di-tert-butyl-fluorene.

10. The method of claim 1 wherein the reacting step of Step III further comprises reacting with a salt of HCl, HBr or HI.

11. The method of claim 10 wherein the salt of HCl, HBr or HI of step III is $(C_2H_5)_4$NI, KBr, NaBr, KI, NaI or CsBr.

12. The method of claim 1 wherein the compound of the Group 10 metal is an anhydrous salt of the Group 10 metal.

13. The method of claim 12 wherein the compound of Group 10 metal of step III is an anhydrous salt of Ni.

14. The method of claim 1 wherein Ra, Rb, and Rc are the same and are tert-butyl.

15. The method of claim 1 wherein the Lewis acid is $AlCl_3$ and the product of Step I includes residual Al.

* * * * *